United States Patent [19]

Mather et al.

[11] Patent Number: 5,166,190
[45] Date of Patent: Nov. 24, 1992

[54] METHOD FOR INCREASING FERTILITY IN MALES

[75] Inventors: Jennie P. Mather, Millbrae; Kenneth M. Attie, San Francisco, both of Calif.

[73] Assignee: Genentech, Inc., South San Francisco, Calif.

[21] Appl. No.: 461,714

[22] Filed: Jan. 8, 1990

[51] Int. Cl.[5] .................. A61K 37/43; C07K 13/00
[52] U.S. Cl. ........................ 514/8; 530/397; 530/399; 514/12
[58] Field of Search ............... 530/350, 399, 397; 514/12, 8

[56] References Cited

U.S. PATENT DOCUMENTS

| 4,734,398 | 3/1988 | diZerega | 514/2 |
| 4,764,502 | 8/1988 | diZerega | 514/2 |
| 4,798,885 | 1/1989 | Mason | 530/350 |
| 4,864,019 | 9/1989 | Vale et al. | 530/387 |

FOREIGN PATENT DOCUMENTS 0178841 4/1986 European Pat. Off.

OTHER PUBLICATIONS

Tsafriri et al., Endocrin., 125:1857–1862 (1989).
Hsueh et al., PNAS USA, 84:5082–5086 (1987).
deKretser & Robertson, Biol. of Reprod., 40:33–47 (1989).
Ignotz & Massague, J. Biol. Chem., 261:4337–4345 (1986).
Adashi & Resnick, Endocrinology, 119:1879–1881 (1986).
Feng et al., J. Biol. Chem., 261:14167–14170 (1986).
Ying et al., BBRC, 136:969–975 (1986).
Hutchinson et al., BBRC, 146:1405–1412 (1987).
Mondschein et al., Endocrinology, 123:1970–1976 (1988).
Carson et al., J. Reprod. Fert., 85:735–746 (1989).
Gonzales-Manchon & Vale, Endocrinology, 125:1666–1672 (1989).
Baird et al., Ann. NY Acad. Sci., 541:153–161 (1988).
DeJong, Physiol. Rev., 68(2):555–607 (1988).
Sheth & Moodbidri, Adv. Contracept., 2:131–139 (1986).
Findlay, Fertil. Steril., 46:770–783 (1986).
Baker et al., Clin. Reprod. & Fertil., 2:161–174 (1983).
Bremner et al., J. Clin. Invest., 68:1044–1052 (1981).
Lee et al., Science 243:396–398 (1989).
Lee et al., in Serono Symposium Publications, entitled "The Molecular and Cellular Endocrinology of the Testis," Cooke & Sharpe, eds., vol. 50 (Raven Press, N.Y., 1988) pp. 21–27.
Van Dissel-Emiliani et al., Endocrinology, 125:1898–1903 (1989).
Bhasin et al., Endocrinology, 124:987–991 (1989).
Roberts et al, Endocrinology, 125:2350–2359 (1989).
Shaha et al., Endocrinology, 125:1941–1950 (1989).
Mather, in Mammalian Cell Culture, ed. J. Mather (Plenum Publishing Corp. 1984), pp. 167–193.

Primary Examiner—Margaret Moskowitz
Assistant Examiner—Shelly J. Guest
Attorney, Agent, or Firm—Janet E. Hasak

[57] ABSTRACT

A method is provided for increasing fertility in a male mammal exhibiting germinal epithelium failure comprising administering to the mammal an effective amount of activin. Preferably, the administration is to the testis of the mammal.

8 Claims, 1 Drawing Sheet

METHOD FOR INCREASING FERTILITY IN MALES

FIELD OF THE INVENTION

This invention relates to a method for increasing fertility in male mammals having a low sperm count.

DESCRIPTION OF RELATED ART

Inhibin is a glycoprotein produced by diverse tissues, including the gonads, pituitary, brain, bone marrow, placenta, and adrenal gland. It was initially identified by its ability to inhibit the secretion of follicle stimulating hormone (FSH) by the pituitary. De Jong and Sharpe, *Nature*, 263: 71–72 (1976); Schwartz and Channing, *Proc. Natl. Acad. Sci. USA*, 74: 5721–5724 (1977). Such preferential regulation of the gonadotropin secretion has generated a great deal of interest and prompted many laboratories in the past fifty years to attempt to isolate and characterize this substance from extracts of testis, spermatozoa, rete testis fluid, seminal plasma, and ovarian follicular fluid using various bioassays. Rivier et al., *Biochem. Biophys. Res. Commun.*, 133: 120 (1985); Ling et al., *Proc. Natl. Acad. Sci. USA*, 82: 7217 (1985); Fukuda et al., *Mol. Cell Endocrinol.*, 44: 55 (1985). The structure of inhibin, characterized from several species, consists of two disulfide-linked subunits: an $\alpha$ and either a $\beta A$ or a $\beta B$ chain.

After the identification of inhibin, activin was shown to exist in follicular fluid as a naturally occurring substance. Activin was found to be capable of stimulating FSH release by rat anterior pituitary cells. Vale et al., *Nature*, 321: 776–779 (1986); Ling et al., *Nature*, 321: 779–782 (1986). Activin consists of a homodimer or heterodimer of inhibin $\beta$ subunits, which may be $\beta_A$ or $\beta_B$ subunits. Vale et al., *Recent Prog. Horm. Res.*, 44: 1–34 (1988). There is 95–100% amino acid conservation of $\beta$ subunits among human, porcine, bovine, and rat activins. The $\beta_A$ and $\beta_B$ subunits within a given species are about 64–70% homologous. The activin $\beta_A$ and $\beta_B$ homodimers ("Activin A" and "Activin B," respectively) have been identified in follicular fluid, and both molecules have been cloned and their genes expressed. Mason et al., *Biochem. Biophys. Res. Commun.*, 135: 957 (1986); EP Pub. No. 222,491 published May 20, 1987; Mason et al., *Molecular Endocrinol.*, 3: 1352–1358 (1989). The complete sequence of the $\beta_B$ subunit is published in Serono Symposium Publications, entitled "Inhibin- Non-Steroidal Regulation of Follicle Stimulating Hormone Secretion", eds. H. G. Burger et al., abstract by A. J. Mason et al., vol. 42, pp. 77–88 (Raven Press: New York 1987), entitled "Human Inhibin and Activin: Structure and Recombinant Expression in Mammalian Cells."

Both Activin A and Activin AB, but thus far not Activin B, have been isolated from natural sources. Activin mRNA ($\beta_A$ and $\beta_B$ subunits), bioactivity, and immunoactivity have been reported to be produced by testicular Leydig cells from immature rat and pig. Lee et al., *Science*, 243: 396–398 (1989); Lee et al., in Serono Symposium Publications, entitled "The Molecular and Cellular Endocrinology of the Testis," Cooke and Sharpe, eds., Vol. 50 (Raven Press: New York, 1988), p. 21–27. Activin A has been found recently to have erythropoietic-stimulating activity as well as FSH-releasing activity. See EP Publ. No. 210,461 published Feb. 4, 1987 (where the protein is called BUF-3), Eto et al., *Biochem. Biophys. Res. Commun.*, 142: 1095–1103 (1987) and Murata et al., *Proc. Natl. Acad. Sci. U.S.A.*, 85: 2434–2438 (1988) (where the activin is called EDF), and Yu et al., *Nature*, 330: 765–767 (1987) (where the activin is called FRP). In these systems, inhibin antagonized the actions of activin.

A protein known as follicle or follicular regulatory protein having a molecular weight of 12,000 to 15,000 is found to inhibit aromatase levels, modulate the formation of mature ova substantially independently of steroidal sex hormones, and reduce fertility in the male rat by systemic treatment. It does not directly affect the gonadotropin output of the pituitary. See U.S. Pat. No. 4,734,398; Tsutsumi et al., *Fertil. Steril.*, 47: 689 (1987); Lew et al., *Obstet. and Gynecol.* 70: 157–162 (1987); diZerega et al., *Meiotic Inhibition: Molecular Control of Meiosis* (Alan R. Liss, Inc., 1988), p. 201–226; diZerega et al., *J. Steroid Biochem.*, 27: 375–383 (1987); Montz et al., *Am. J. Obstet. Gynecol.*, 436–441 (Feb. 15, 1984); Ahmad et al., *the Anatomical Record.* 224: 508–513 (1989). This protein, also named FRP, has been purified and partially sequenced, and is not related in any way to the FSH-releasing protein known as activin, referred to as FRP by the Salk researchers in their early work.

Recently, the expression of inhibin subunits, each encoded by a separate gene, was demonstrated in several tissues in addition to ovary and testis. Inhibin $\alpha$, $\beta_A$, and $\beta_B$ mRNAs were detected in placental, pituitary, adrenal, bone marrow, kidney, spinal cord, and brain tissues. Meunier et al., *Proc. Natl. Acad. Sci. USA*, 85: 247 (1988). The expression of the inhibin subunit mRNAs varied by several-fold in a tissue-specific manner, suggesting different functions for these proteins depending on their pattern of association and their site of production.

Inhibin and activin are members of a family of growth and differentiation factors. The prototype of this family is transforming growth factor-beta (TGF-$\beta$) (Derynck et al., *Nature*, 316: 701–705 (1985)), Which, according to one source, possesses FSH-releasing activity. Ying et al., *Biochem. Biophys. Res. Commun.*, 135: 950–956 (1986). Other members of the TGF-$\beta$ family include the Mullerian inhibitory substance, the fly decapentaplegic gene complex, and the product of Xenopus Vg-1 mRNA.

In the human, growing preovulatory follicles and corpus luteum secrete inhibin into the circulation in response to FSH stimulation. Lee and Gibson, *Aust. J. Biol. Sci.*, 38: 115–120 (1985); McLachlan et al., *Fertil. Steril.*, 48: 1001 (1987). Thus, inhibin-related peptides play important roles in the modulation of gonadal functions via a pituitary feedback loop. In rat primary cultures of testis cells and ovarian thecal-interstitial cells, inhibin has been reported to enhance androgen biosynthesis stimulated by leutinizing hormone (LH), whereas activin suppresses androgen production. Hsueh et al., *Proc. Natl. Acad. Sci. USA*, 84: 5082–5086 (1987). Other workers have been unable to repeat these observations. deKretser and Robertson, *Biology of Reproduction*, 40: 33–47 (1989), particularly p. 41. Inhibitory effects of TGF-$\beta$ on Leydig cell steroidogenesis have also been described. Lin et al., *Biochem. Biophys. Res. Commun.*, 146: 387 (1987); Fauser and Hsueh, *Life Sci.*, 43: 1363 (1988); Avallet et al., *Biochem. Biophys. Res. Commun.*, 146: 575 (1987). In granulosa cells, activin has been reported to inhibit (and TGF-$\beta$ to enhance) progesterone production. Ignotz and Massague, *J. Biol. Chem.*, 261: 4337 (1986). In primary cultures of granulosa cells, activin and inhibin as well as TGF-β were found to affect hormone synthesis and secretion, each in a different fashion. Adashi and Resnick, *Endocrinology*, 119: 1879 (1986); Ying et al., *Biochem. Biophys. Res. Commun.*, 136: 969 (1986); Hutchinson et al., *Biochem. Biophys. Res. Commun.*, 146: 1405 (1987); Mondschein et al., *Endocrinology*, 123: 1970 (1988); Feng et al., *J. Biol. Chem.*, 261: 14167 (1986). These molecules have both positive and negative effects on FSH-dependent granulosa cell function. Carson et al., *J. Reprod. Fert.*, 85: 735-746 (1989). Also suggested is that individual members of the TGF-β/inhibin gene family regulate ovarian function, not only by direct action on follicle cells, but also indirectly by influencing the production rate of other members of that family. Zhiwen et al., *Molecular and Cellular Endocrinology*. 58: 161-166 (1988).

Activin A and inhibin were reported to modulate growth of two gonadal cell lines, suggesting that these proteins may regulate proliferation as well as functions of gonadal cells. Gonzalez-Manchon and Vale, *Endocrinology*. 125: 1666-1672 (1989). The secretion of inhibin by the corpus luteum has been proposed to suppress the concentration of FSH in the luteal phase of the cycle and hence the inhibition of follicular development. Baird et al., *Ann. N. Y. Acad. Sci.*, 541: 153-161 (1988).

A review article postulates that inhibin is at least one of the factors that determines the number of follicles destined to ovulate, and that interference with the action of inhibin might contribute to the regulation of fertility. De Jong, *Physiol. Rev*, 68: 555 (1988). Many investigators have speculated that due to its FSH-inhibiting effect, inhibin may be useful in male and female contraception. Sheth and Moodbidri, *Adv. Contracept.* 2: 131-139 (1986); Findlay, *Fertil. Steril.*. 46: 770 (1986); van Dissel-Emiliani et al., *Endocrinology*, 125: 1898-1903 (1989); Bhasin et al., *Endocrinology*, 124: 987-991 (1989). However, another author doubts that inhibin can inhibit spermatogenesis (citing Bremner et al., *J. Clin. Invest.*, 68: 1044 (1981)), and states that inhibin might also have some direct stimulatory effects on spermatogenesis. Baker et al., *Clin. Reprod. and Fert.*, 2: 161-174 (1983).

The distributions of the α, β_A, and β_B subunits of inhibin/activin polypeptides were studied in the testis of rats. It was found that in the rat testis, both Sertoli and interstitial cells produce inhibin/activin subunits, and the α and β subunits are produced by different types of interstitial cells in immature rats. Roberts et al., *Endocrinology*, 125: 2350 (1989). Also it was found that immunoreactive inhibin subunits are present in multiple cells in the testis and that the amounts of immunostainable subunits in the seminiferous epithelium are differentially regulated. Shaha et al., *Endocrinology*. 125: 1941 (1989).

Activin bioactivity has been reported to be secreted by interstitial cells in vitro, while Sertoli cells secrete inhibin or a mixture of inhibin and activin. Lee et al., in Serono Symposium Publications, supra; Lee et al., *Science*. supra.

Many substances produced in the testes have been shown to regulate testicular function locally. Mather, in *Mammalian Cell Culture*. ed. J. Mather (Plenum Publishing Corp. 1984), p. 167-193. While inhibin and activin have primarily been considered as feedback regulators of pituitary function, in light of recent data on multiple sites of production and action in the testis, it seems likely that they may also play a role as local regulators of testicular function.

Failure to conceive is a complaint that leads as many as one in six married couples to seek medical attention. Of these couples, at least 40% will be discovered to have a male factor deficiency. Approximately 61% of infertile men have hypospermatogenesis on testicular biopsy. These patients have partial germinal epithelium failure and present with oligospermia and normal testosterone levels. The etiology is often idiopathic, but may be associated with antineoplastic agents, cryptorchidism, or varicoceles.

In the male, the maturation of immature germ cells into spermatozoa (spermatogenesis) is thought to be regulated by the gonadotropins (LH and especially FSH) and androgens (testosterone). The current treatments for male infertility due to oligospermia are based on this assumption. These include induction of rebound from testosterone or anabolic androgen-induced azospermia; administration of exogenous gonadotropins or gonadotropin releasing hormone; use of clomiphene citrate or tamoxifen to stimulate endogenous gonadotropin secretion; administration of low doses of mesterolone, an oral synthetic androgen; and use of an aromatase inhibitor such as testolactone.

No study has conclusively established the benefit of these treatments, although one report suggests that a statistically significant effect is exerted only by clomiphene citrate. However, clomiphene has been shown to be problematic in the high doses used by women. Furthermore, the gonadotropins and androgens may act primarily in an indirect manner, via stimulation of Sertoli and/or Leydig cell factors that affect the germinal epithelium directly.

Accordingly, it is an object of the present invention to provide a method for increasing fertility of men with oligospermia using a fertility agent that causes direct stimulation of sperm production by local administration.

It is another object to provide a fertility agent to treat hypospermatogenesis that is both safe and efficacious.

This object and other objects will be apparent to one of ordinary skill in the art.

SUMMARY OF THE INVENTION

The present invention provides a method of increasing fertility in a male mammal exhibiting germinal epithelium failure comprising administering to the mammal an effective amount of activin.

In another aspect, the invention provides a pharmaceutical composition for increasing fertility in male mammals exhibiting germinal epithelium failure comprising an effective amount of activin in a pharmaceutically acceptable carrier.

DESCRIPTION OF THE PREFERRED EMBODIMENTS

As used herein, the term "activin" refers to homo- or heterodimers of $\beta$ chains of inhibin, prepro forms, and pro forms, together with glycosylation and/or amino acid sequence variants thereof. After cleavage from the mature protein, the precursor portion may be non-covalently associated with the mature protein. Activin A refers to activin with the two chains of $\beta_A$. Activin AB refers to activin with the chains $\beta_A$ and $\beta_B$. Activin B refers to activin with the two chains of $\beta_B$.

The intact isolated prepro or prodomain or mature $\beta_A$ and $\beta_B$ sequences are suitably synthesized by any means, including synthetic and/or recombinant means, but are preferably synthesized in recombinant cell culture, for example, as described in U.S. Pat. No. 4,798,885 issued Jan. 17, 1989.

Figure 2A:
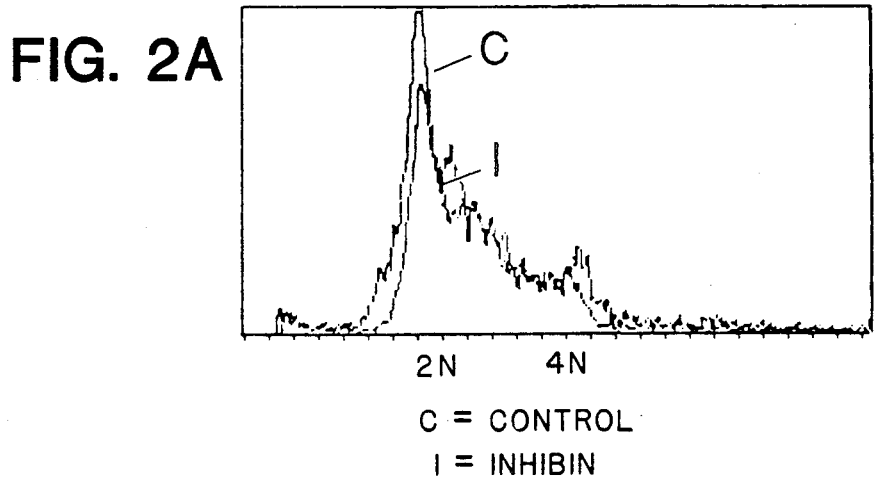
FIG. 2A shows a graph of DNA flow cytometric quantification of inhibin-treated rat Sertoli and germ cell cocultures at 48 hours compared with a control (5F).
Figure 2B:
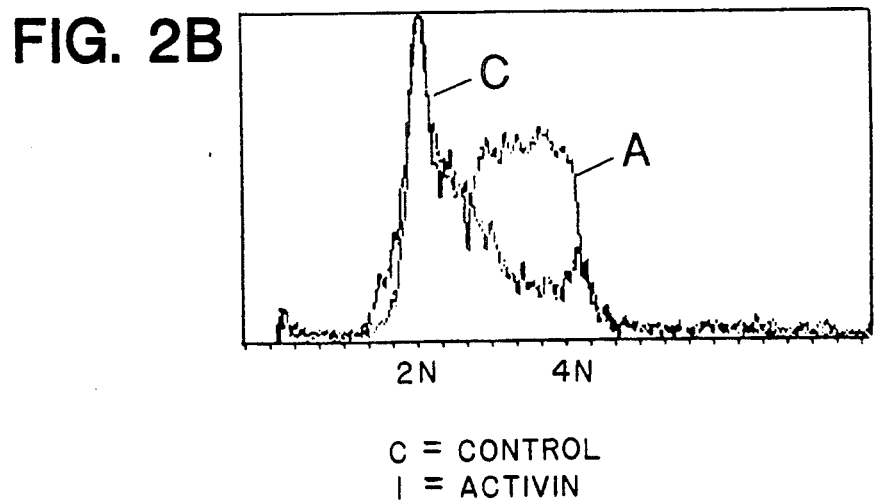
FIG. 2B shows a similar graph comparing activin treatment with a control (5F).

It is within the scope hereof to employ activin from animals other than humans, for example, porcine or bovine sources, to treat humans. For example, the nucleotide and deduced amino acid sequences of the porcine activin $\beta$ chain are found in FIGS. 2A and 2B of U.S. Pat. No. 4,798,885, supra. Likewise, if it is desirable to treat other mammalian species such as domestic and farm animals and sports, zoo, or pet animals, human activin, as well as activin from other species, is suitably employed.

Generally, amino acid sequence variants will be substantially homologous with the relevant portion of the mammalian $\beta$ chain sequences set forth in, e.g., U.S. Pat. No. 4,798,885, supra. Substantially homologous means that greater than about 60% of the primary amino acid sequence of the homologous polypeptide corresponds to the sequence of the activin chain when aligned to maximize the number of amino acid residue matches between the two proteins. Alignment to maximize matches of residues includes shifting the amino and/or carboxyl terminus, introducing gaps as required, and/or deleting residues present as inserts in the candidate. Typically, amino acid sequence variants will be greater than about 70% homologous with the corresponding native sequences.

While the site for introducing a sequence variation is predetermined, it is unnecessary that the mutation per se be predetermined. For example, in order to optimize the performance of mutation at a given site, random mutagenesis may be conducted at the target codon or region and the expressed activin mutants screened for the optimal combination of desired activity. Techniques for making substitution mutations at predetermined sites in DNA having a known sequence are well known, for example, M13 primer mutagenesis.

Mutagenesis is conducted by making amino acid insertions, usually on the order of about from 1 to 10 amino acid residues, or deletions of about from 1 to 30 residues. Substitutions, deletions, insertions, or any subcombination may be combined to arrive at a final construct. Preferably, however, substitution mutagenesis is conducted. Obviously, the mutations in the encoding DNA must not place the sequence out of reading frame and preferably will not create complementary regions that could produce secondary mRNA structure.

Covalent modifications of activin are included within the scope of the invention, and include covalent or aggregative conjugates with other chemical moieties. Covalent derivatives are prepared by linkage of functionalities to groups that are found in the activin amino acid side chains or at the N- or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as aryl or alanyl; and N-acyl derivatives of the amino terminal amino acid or amino-group containing residues, e.g., lysine or arginine. The acyl group is selected from the group of alkyl moieties (including C3 to C10 normal alkyl), thereby forming alkanoyl species, and carbocyclic or heterocyclic compounds, thereby forming aroyl species. The reactive groups preferably are difunctional compounds known per se for use in crosslinking proteins to insoluble matrices through reactive side groups, e.g., m-maleimido-benzoyl-N-hydroxy succinimide ester. Preferred derivatization sites are at histidine residues.

The expression "administering to the testis" means not only injection into the testis, but also techniques that result in flooding the area surrounding the testis with activin such that the activin is absorbed into the testis. In addition, the activin can be injected into a vessel that feeds the testis, preferably using a microscopic procedure. Furthermore, the activin can be put into an implant that is placed near the testis and through which the activin is absorbed into the testis. Examples include an intratesticular long-acting depot (e.g., microsphere) or slow-release implant. Other techniques may be employed, provided that the result is that activin is applied locally to the testis and is effective for the purposes stated herein.

The expression "germinal epithelium failure" refers to disorders of male mammals that may be characterized as complete or partial germinal epithelium failure, provided that some spermatogonal stem cells are present, as determined, e.g., by a testis biopsy analysis. Examples of such disorders include those characterized as partial germinal epithelium failure as well as azoospermia presenting in patients who have some spermatogonal stem cells. Complete failure is associated with high basal FSH levels.

The expression "partial germinal epithelium failure" refers to a disorder of mammals that present with oligospermia and intact Leydig cell steroidogenic capacity and pituitary cells. Such males have normal testosterone levels but low sperm counts. Most clinicians consider a sperm density of less than 20 million/ml with adequate volume, motility and morphology to indicate low sperm count. Sperm morphology is another indication, with one suggestion that low sperm count is evidence when the percentage of abnormal spermatozoa is above 40.

The disorders characterized as partial germinal epithelium failure may be caused by chemicals or drugs such as chemotherapeutic drugs and sulfa antibiotics, as well as alcohol and illicit drugs. Other possible causes include genetic disorders, genital tract infections, and varicoceles. The largest group of infertile men falls into the category of idiopathic oligospermia, without an evident etiology. The need for an increase in fertility is generally due to a primary testicular disorder, i.e., not at the hypothalamic or pituitary level.

The present invention concerns itself with using activin to increase fertility in male mammals in the patient population identified above, including sports, zoo, pet, and farm animals such as dogs, cats, cattle, pigs, horses, monkeys, and sheep, as well as humans. Preferably the disorder is partial germinal epithelium failure.

The activin is administered to the mammal by any suitable technique, including parenteral, sublingual, intratesticular, intrapulmonary, and intranasal administration. The specific route of administration will depend, e.g., on the medical history of the patient. Examples of parenteral administration include intramuscular, subcutaneous, intravenous, intraarterial, and intraperitoneal administration. Preferably, the activin is administered via the testis, as discussed above.

The activin compositions to be used in the therapy will be formulated and dosed in a fashion consistent with good medical practice, taking into account the clinical condition of the individual patient, the site of delivery of the activin composition, the method of administration, the scheduling of administration, and other factors known to practitioners. The "effective amount" for purposes herein is thus determined by such considerations.

As a general proposition, the total pharmaceutically effective amount of the activin administered per dose will be in the range of about 1 µg/kg/day to 10 mg/kg/day of patient body weight, although, as noted above, this will be subject to a great deal of therapeutic discretion. Preferably, this dose is no more than about 10 µg/kg/day. The key factor in selecting an appropriate dose is the result obtained, as measured by increases in sperm density by serum analysis or the number of spermatocytes, or by other criteria as deemed appropriate by the practitioner, e.g., biopsy.

For administration, the activin is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the activin uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, nitrate, and other organic acid salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as Tween, Pluronics, or PEG.

The activin is typically formulated in such vehicles at a concentration of about 0.1 mg/ml to 100 mg/ml at physiological pH. It will be understood that use of certain of the foregoing excipients, carriers, or stabilizers will result in the formation of activin salts.

Activin to be used for therapeutic administration must be sterile. Sterility is readily accomplished by filtration through sterile filtration membranes (e.g., 0.2 micron membranes).

Therapeutic activin compositions generally are placed into a container having a sterile access port, for example, a vial having a stopper pierceable by a hypodermic injection needle.

Activin ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous activin solution, and the resulting mixture is lyophilized. The infusion solution is prepared by reconstituting the lyophilized activin using 5 ml of sterile water or Ringer's solution.

The activin is also suitably administered by sustained release systems. Suitable examples of sustained release compositions include semi-permeable polymer matrices in the form of shaped articles, e.g., films, or microcapsules. Sustained release matrices include polylactides (U.S. Pat. No. 3,773,919, EP 58,481), copolymers of L-glutamic acid and gamma-ethyl-L-glutamate (U. Sidman et al., *Biopolymers,* 547–556 (1983)), poly(2-hydroxyethyl methacrylate) (R. Langer et al., *J. Biomed. Mater. Res.,* 15: 167–277 (1981), and R. Langer, *Chem. Tech.,* 12: 98–105 (1982)), ethylene vinyl acetate (R. Langer et al., Id.) or poly-D-(—)-3-hydroxybutyric acid (EP 133,988). Sustained release activin compositions also include liposomally entrapped activin. Liposomes containing activin are prepared by methods known per se: DE 3,218,121; Epstein et al., *Proc. Natl. Acad. Sci. U.S.A.,* 82: 3688–3692 (1985); Hwang et al., *Proc. Natl. Acad. Sci. U.S.A.,* 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal activin therapy.

Activin therapy is suitably combined with other proposed or conventional fertility increasing therapies. For example, activin can be administered with other fertility agents used to stimulate proliferation and differentiation of germ cells.

Examples of other therapies or agents include induction of rebound from testosterone or anabolic androgen-induced azospermia; administration of exogenous gonadotropins or gonadotropin releasing factors such as human chorionic gonadotropin (hCG), human menopausal gonadotropin (hMG), purified FSH, or gonadotropin releasing hormone (GnRH). Alteratively, clomiphene citrate or tamoxifen may be used in conjunction with activin to stimulate endogenous gonadotropin secretion. In addition, low doses of mesterolone, an oral synthetic androgen, or an aromatase inhibitor such as testolactone may be administered.

The inhibin and fertility agents are suitably delivered by separate or the same means, by separate or the same administration route, and at the same or at different times, depending, e.g., on dosing, the clinical condition of the patient, etc. It is not necessary that such fertility agents be included in the activin compositions per se, although this will be convenient Where such drugs are delivered by the same administration route.

When employed together with the activin, such agents typically are employed in lesser dosages than when used alone. If hCG is used, preferably the effective amount is 1500 to 2000 I.U. twice weekly until testosterone levels are in the adult male range. At that point, hMG in a dose of about one ampule every other day is also administered. If clomiphene citrate therapy is employed, treatment is typically 25 mg of clomiphene citrate daily for 21 to 25 days, followed by a 5- to 7-day rest period. This cycle is generally repeated for at least 24 weeks.

A typical combined composition will contain the above-noted amount of activin and about 25 mg of clomiphene citrate in a suitable intraperitoneal fluid such as lactated Ringer's solution.

The invention will be more fully understood by reference to the following examples. They should not, however, be construed as limiting the scope of the invention. All literature and patent citations are expressly incorporated by reference.

EXAMPLE I

Sertoli cells and germ cells from 20-day-old male Sprague-Dawley rats (Charles River Laboratories, Inc., Wilmington, Mass.) were co-cultured in serum-free media. Cultures were prepared according to the glycine/collagenase method described by Mather and Phillips in *Methods for Serum-Free Culture of Cells of the Endocrine System*, Barnes and Sato eds. (Alan R. Liss, Inc.: New York, 1984), p. 29–45, and Rich et al., *Endocrinol.*, 113: 2284–2293 (1983).

Briefly, testis were removed and decapsulated and the tubules teased apart in a hypertonic glycine solution. The return of the tubules to isoosmotic medium results in lysis of the interstitial tissue without harming the tubules. The tubules were then minced into smaller segments and enzymatically treated with collagenase/dispase to remove the basement membranes and peritubular cells. The peritubular cells were discarded and the tubular pieces of 1–5 mm in length, which contain Sertoli cells and spermatogonia and spermatqcytes, were plated in serum-free Ham's F12/DME medium supplemented with HEPES and insulin, 5 µg/ml; transferrin, 5 µg/ml; α-tocopherol, 5 µg/ml; epidermal growth factor (EGF), 5 ng/ml; and aproteinin, 25 µg/ml (5F). After 20–24 hours the Sertoli cells had attached to the substrate and spread to form a monolayer. Spermatocytes could be seen adhering to the monolayer as single cells or groups of two cells or floating unattached in the medium.

At 24 hours after plating the medium was changed and unattached cells were discarded. Fresh 5F medium was added to all cultures, and additionally 100 ng/ml human recombinant inhibin A or activin A (prepared and purified as described in U.S. Pat. No. 4,798,885 issued Jan. 17, 1989) was added to the experimental cultures. All cultures were assayed in triplicate and the entire experiment was repeated multiple (>10) times.

Between 24 and 48 hours of treatment, clusters of spermatogonia and increased numbers of primary spermatocytes appeared in the activin-treated wells. These cells appear as connected clusters of 8–32 cells attached to the Sertoli cell monolayer and large cells in suspension. No such effect was seen with inhibin.

Each well contained 2 million cells. A total of 1 µCi of 3H-thymidine was added to each well after 24, 48, or 72 hours of treatment with activin or inhibin.

Label incorporation into cells was measured after 20 hours of incubation with 3H-thymidine. Cells were detached from the substrate by vigorous pipetting with a 1 ml Pipettman TM pipettor, and the entire contents of the well was transferred to a 10-ml filter well containing two glass fiber filters and 5 ml of cold 20% trichloroacetic acid. The precipitated cells were caught on the filter and washed two times with cold 5% trichloroacetic acid to remove unincorporated 3H-thymidine. Filters were washed once with cold methanol and counted in a scintillation fluid appropriate for aqueous samples.

Figure 1:
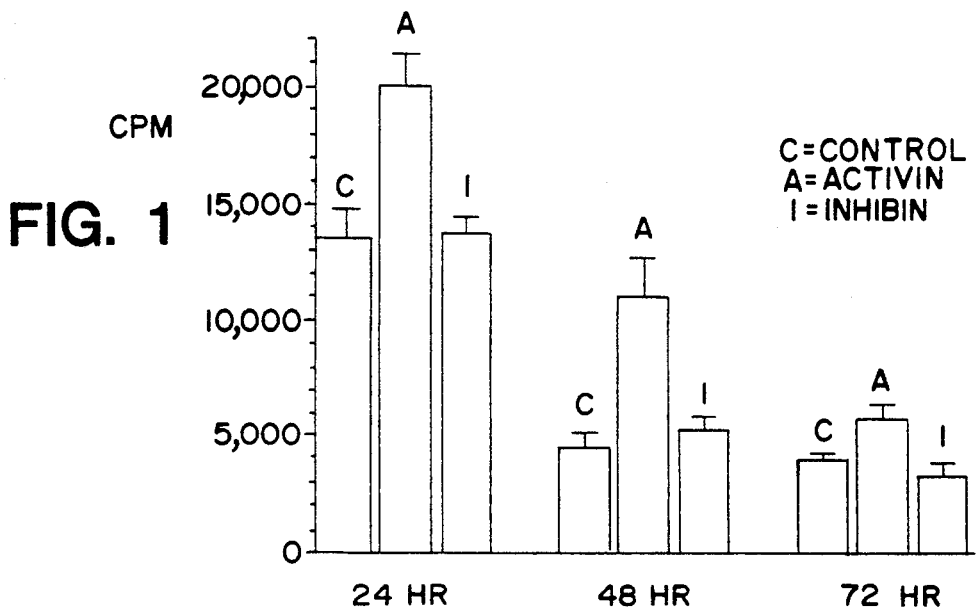
FIG. 1 shows graphs of the level of incorporation of 3H-thymidine after 24 hours, 48 hours and 72 hours of treatment of rat Sertoli and germ cell cocultures with added activin A (A, 100 ng/ml), added inhibin (I, 100 ng/ml), or control (C). All cultures contained medium plus 5F (which is insulin, 5 μg/ml; transferrin, 5 μg/ml; α-tocopherol, 5 μg/ml; EGF, 5 ng/ml; and aproteinin, 25 μg/ml).

The results are shown in FIG. 1. Incorporation was higher in the activin-treated wells compared with untreated control or inhibin-treated wells in all cases. At 48 hours of culturing the activin was at its highest incorporation (11,040 cpm±1572 SEM) relative to the control (4515±597) and inhibin-treated cultures (5355±466). Thus, activin increases the proliferation of the spermatocytes.

The effect of inhibin and activin on germ cell differentiation was quantified by flow cytometric analysis. Sertoli cells were stained with Nile red (a selective fluorescent stain for intracellular lipid droplets) and non-staining germ cells were electronically gated. A DNA-specific fluorochrome (Hoechst 33342) was used to determine the percentage of germ cells with N, 2N or 4N DNA content, with 4N=primary spermatocytes. As seen from FIGS. 2A and 2B, activin-treated cultures had a significant increase in the percentage of 4N germ cells as compared with control or inhibin-treated cultures at 48 hours.

In conclusion, activin stimulates the proliferation and differentiation of 20-day old rat testicular germ cells in vitro, indicating that it will increase fertility in the male. The data also indicate that local administration of activin, being mitogenic for germ cells via, e.g., an intratesticular depot method, would cause direct gonadal stimulation of sperm production, independent of (or possibly in concert with) changes in gonadotropin secretion.

What is claimed is:

1. A method of increasing fertility in a male mammal exhibiting germinal epithelium failure comprising administering to the mammal an effective for increasing fertility in male mammals amount of activin.

2. The method of claim 1 wherein the activin is porcine or human activin A, activin AB, or activin B.

3. The method of claim 2 wherein the activin is human activin A.

4. The method of claim 1 wherein the administration is to the testis.

5. The method of claim 4 wherein the administration is by injection into the testis.

6. The method of claim 1 wherein the mammal is human.

7. The method of claim 1 wherein the effective amount is a daily dose of about 1 µg/kg to 10 mg/kg.

8. The method of claim 1 wherein the germinal epithelium failure is partial germinal epithelium failure.

* * * * *